(12) United States Patent
Cronin et al.

(10) Patent No.: US 10,229,754 B2
(45) Date of Patent: Mar. 12, 2019

(54) WEARABLE DEVICE OBTAINING AUDIO DATA FOR DIAGNOSIS

(71) Applicant: KONINKLIJKE PHILIPS N.V., Eindhoven (NL)

(72) Inventors: John E. Cronin, Bonita Springs, FL (US); Steven M. Philbin, Tuscaloosa, AL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/552,383

(22) PCT Filed: Mar. 8, 2016

(86) PCT No.: PCT/EP2016/054837
§ 371 (c)(1),
(2) Date: Aug. 21, 2017

(87) PCT Pub. No.: WO2016/142360
PCT Pub. Date: Sep. 15, 2016

(65) Prior Publication Data
US 2018/0035901 A1    Feb. 8, 2018

Related U.S. Application Data

(60) Provisional application No. 62/130,226, filed on Jun. 9, 2015.

(30) Foreign Application Priority Data

Jul. 20, 2015  (EP) .................................... 15177458

(51) Int. Cl.
*G16H 40/63*       (2018.01)
*A61B 5/024*       (2006.01)
(Continued)

(52) U.S. Cl.
CPC ............... *G16H 40/63* (2018.01); *A61B 5/00* (2013.01); *A61B 5/0022* (2013.01); *A61B 5/0024* (2013.01); *A61B 5/02055* (2013.01); *A61B 5/02438* (2013.01); *A61B 5/6801* (2013.01); *A61B 5/746* (2013.01); *G06F 19/00* (2013.01); *G06F 19/3418* (2013.01); *A61B 5/021* (2013.01); *A61B 5/024* (2013.01);
(Continued)

(58) Field of Classification Search
CPC ............... A61B 5/02055; A61B 5/0022; A61B 5/02438; A61B 5/746; G06F 19/3418; G16H 40/63
USPC ..................................................... 340/539.12
See application file for complete search history.

(56) References Cited

U.S. PATENT DOCUMENTS 7,733,224 B2 *  6/2010  Tran ..................... G06F 19/3418
                                                        340/540
9,723,997 B1 *  8/2017  Lamego ............... A61B 5/0205
(Continued)

*Primary Examiner* — John A Tweel, Jr.
(74) *Attorney, Agent, or Firm* — Michael W. Haas

(57) ABSTRACT

Systems, devices, and methods for providing audio database for health systems that may utilize wearable devices that monitor wearable sensor readings for symptoms associated with a disease and that may prompt a user of the wearable device to place a microphone from the wearable device on a specific location on the user's body for recording an audio file that may be sent to a health professional for diagnosis of the disease.

14 Claims, 16 Drawing Sheets

(51) Int. Cl.
    *A61B 5/00*     (2006.01)
    *G06F 19/00*     (2018.01)
    *A61B 5/0205*     (2006.01)
    *A61B 5/021*     (2006.01)
    *A61B 5/08*     (2006.01)
    *A61B 5/11*     (2006.01)
    *A61B 5/145*     (2006.01)

(52) U.S. Cl.
    CPC ........... *A61B 5/0816* (2013.01); *A61B 5/0823* (2013.01); *A61B 5/11* (2013.01); *A61B 5/14532* (2013.01); *A61B 5/14542* (2013.01); *A61B 5/681* (2013.01); *A61B 2560/0242* (2013.01)

(56) References Cited

U.S. PATENT DOCUMENTS

| | | |
|---|---|---|
| 2008/0001735 A1 | 1/2008 | Tran |
| 2012/0293323 A1 | 11/2012 | Kaib et al. |
| 2013/0072145 A1 | 3/2013 | Dantu |
| 2014/0278220 A1 | 9/2014 | Yuen |
| 2014/0378810 A1 | 12/2014 | Davis et al. |

* cited by examiner

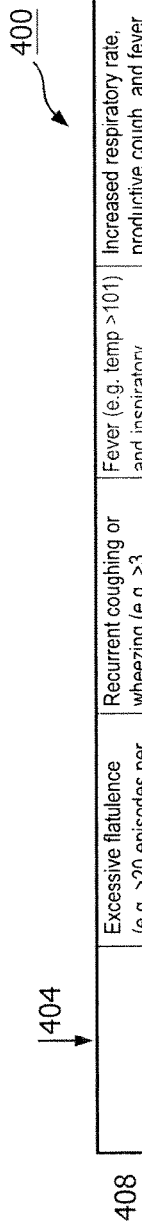

FIG. 4

| 404 → | Excessive flatulence (e.g. >20 episodes per day) | Recurrent coughing or wheezing (e.g. >3 episodes per day for >3 days) | Fever (e.g. temp >101) and inspiratory "Whoop" | Increased respiratory rate, productive cough, and fever (e.g. temp >101) | Frequent waking from sleep (>5 episodes per hour of sleep) |
|---|---|---|---|---|---|
| Aerophagia | Put microphone on throat to listen for excessive air swallowing during eating/drinking  410 | | | | |
| Asthma | | Put microphone on chest to listen to lungs for airflow obstruction  410 | | | |
| Pertussis (Whooping cough) | | | Record cough  410 | | |
| Pneumonia | | | | Put microphone on chest to listen for bronchial breathing and crackles  410 | |
| COPD | | Put microphone on chest to listen to lungs for airflow obstruction  410 | | | |
| Sleep apnea | | | | | Use microphone to record breathing/snoring of the nose and mouth  410 |

408 →

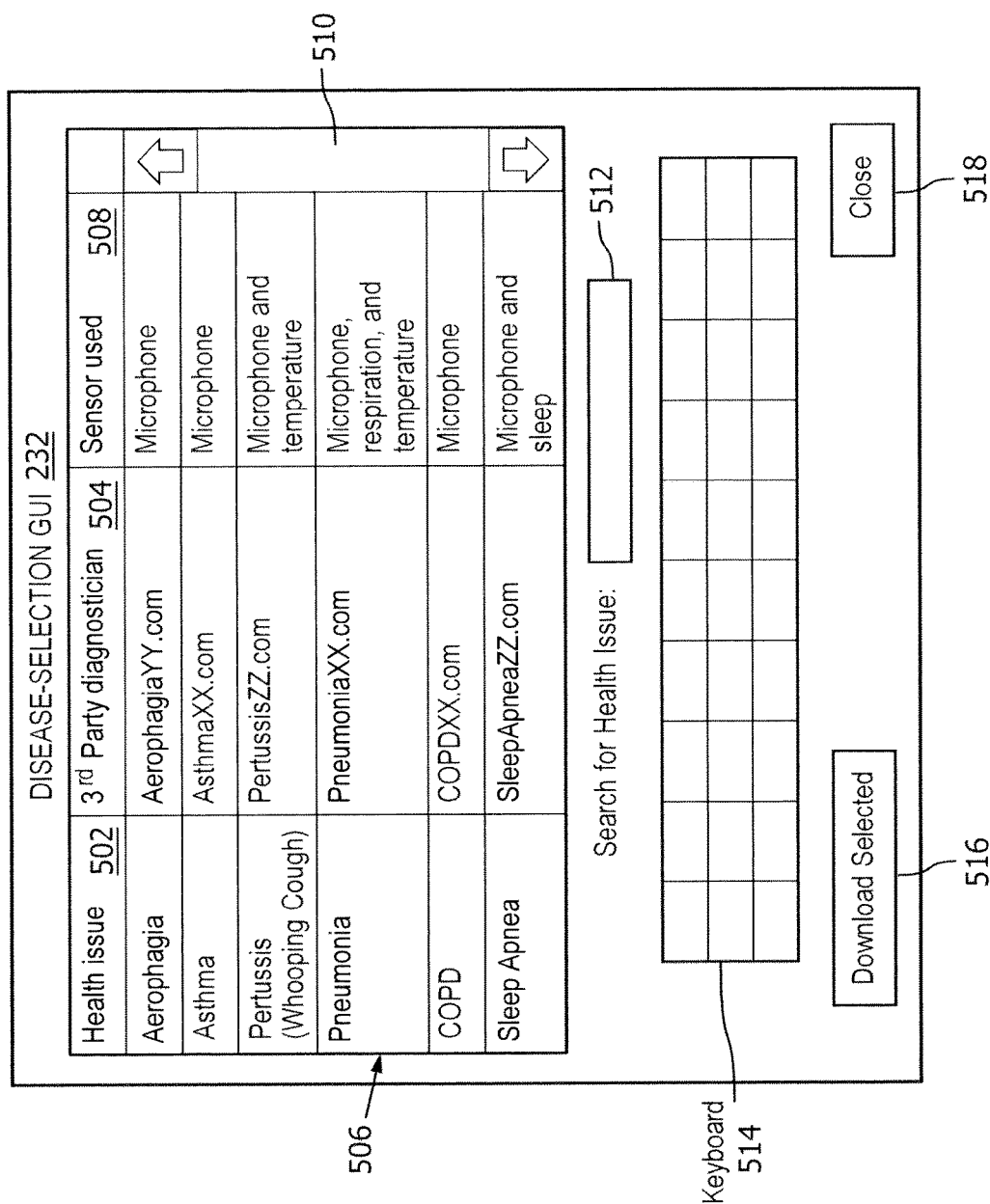

NETWORK DOWNLOAD DB 246

| Health issue 704 | 3rd Party diagnostician 708 | Sensor used 712 | Network alert DB 714 |
|---|---|---|---|
| Aerophagia | AerophagiaYY.com | Microphone | Aerophagia DB |
| Asthma | AsthmaXX.com | Microphone | Asthma DB |
| Pertussis (Whooping Cough) | PertussisZZ.com | Microphone and temperature | Pertussis DB |
| Pneumonia | PneumoniaXX.com | Microphone, respiration, and temperature | Pneumonia DB |
| COPD | COPDXX.com | Microphone | COPD DB |
| Sleep Apnea | SleepapneaZZ.com | Microphone and sleep | Sleep apnea DB |
| ooo | ooo | ooo | ooo |

WEARABLE SENSOR DB 224

| Date | Time | Pulse | Blood pressure | Microphone | Respiration | Temperature | Cough/wheeze total in past 72 hours |
|---|---|---|---|---|---|---|---|
| 02/18/15 | 08:15:20 | 85bpm | 120/80mmHg | N/A | 22resp/min | 101.2°F | 4 |
| 02/18/15 | 08:15:40 | 85bpm | 122/80mmHg | N/A | 22resp/min | 101.2°F | 4 |
| 02/18/15 | 08:16:00 | 86bpm | 120/80mmHg | N/A | 22resp/min | 101.2°F | 4 |
| 02/18/15 | 08:16:20 | 85bpm | 121/80mmHg | N/A | 22resp/min | 101.2°F | 4 |
| 02/18/15 | 08:16:40 | 85bpm | 121/80mmHg | N/A | 22resp/min | 101.2°F | 4 |
| 02/18/15 | 08:17:00 | 86bpm | 120/80mmHg | N/A | 22resp/min | 101.2°F | 4 |
| 02/18/15 | 08:17:20 | 85bpm | 120/80mmHg | N/A | 22resp/min | 101.2°F | 4 |
| 02/18/15 | 08:17:40 | 85bpm | 120/80mmHg | Productive cough | 22resp/min | 101.2°F | 5 |

FIG. 10A

WEARABLE MICROPHONE RECORDING DB 222

| Date | Time | Microphone recording |
|---|---|---|
| 02/18/15 | 08:18:00 | Pneumonia1.wav |
| -- | -- | -- |
| -- | -- | -- |
| -- | -- | -- |
| -- | -- | -- |
| -- | -- | -- |
| -- | -- | -- |

WEARABLE DEVICE OBTAINING AUDIO DATA FOR DIAGNOSIS

CROSS-REFERENCE TO PRIOR APPLICATIONS

This application is the U.S. National Phase application under 35 U.S.C. § 371 of International Application No. PCT/EP2016/054837, filed on Mar. 8, 2016, which claims the benefit of European Application Serial No. 15177458.5, filed Jul. 20, 2015, and of U.S. Provisional Application Ser. No. 62/130,226, filed Mar. 9, 2015. These applications are hereby incorporated by reference herein, for all purposes.

TECHNICAL FIELD

Various embodiments described herein relate generally to the field of wearable devices. More particularly, but not exclusively, various embodiments are directed to wearable devices with an audio database for health.

BACKGROUND

Reducing unnecessary visits to medical offices can reduce healthcare costs, however, many diseases require auscultation by a health professional for diagnosis. In addition, early diagnosis of a medical condition can improve long-term health and reduce healthcare costs, but individuals may be reluctant to visit a health professional, or may think their health issues are not serious enough to warrant a visit to a medical office.

Some wearable devices have been developed to promote access to healthcare and facilitate diagnosis of disease, however, existing devices are not adequately designed for providing early detection for a variety of diseases, including diseases requiring auscultation for diagnosis.

SUMMARY OF THE DISCLOSURE

Aspects of the present disclosure may include systems, devices, and methods for providing early diagnosis of diseases requiring auscultation for diagnosis, and for minimizing unnecessary visits to medical offices by providing confirmation a user does or does not have a disease without needing to visit a medical office. In some embodiments, the present disclosure may include wearable devices configured to monitor a user's vital signs and/or body data to determine whether a user is exhibiting symptoms of a disease, and if the user is exhibiting symptoms, instructing the user to use a microphone from the wearable device to obtain audio data for transmission to a diagnostician for auscultation and diagnosis.

In one implementation, the present disclosure is directed to a method of diagnosing a disease using a wearable device worn by a user, the wearable device having a display and wearable sensors, the wearable sensors including at least one microphone. The method includes monitoring, with the wearable device, wearable sensor data generated by the wearable sensors; comparing, with the wearable device, the wearable sensor data to one or more disease-specific alert settings; notifying a user, with the wearable device, that the user is exhibiting symptoms of a disease when the wearable sensor data meets or exceeds the one or more disease-specific alert settings; and instructing the user, with the wearable device, to place the at least one microphone on a specific location on the user's body for obtaining audio data for auscultation for diagnosing whether the user has the disease.

In another implementation, the present disclosure is directed to a wearable device for diagnosing a disease that includes a display, wearable sensors including at least one microphone, and a machine-readable storage medium for storing machine executable instructions designed and configured to cause the wearable device to: monitor wearable sensor data generated by the wearable sensors; compare the wearable sensor data to one or more disease-specific alert settings; if the wearable sensor data meets or exceeds the one or more disease-specific alert settings, then display an alert message on the display indicating the user is exhibiting symptoms of a disease; and display instructions on the display for placing the at least one microphone on a specific location on the user's body for obtaining audio data for auscultation and diagnosis.

Various embodiments described herein relate to a method of diagnosing a disease using a wearable device worn by a user, the wearable device having a display and wearable sensors, the wearable sensors including at least one microphone, the method including: monitoring, with the wearable device, wearable sensor data generated by the wearable sensors; analyzing, with the wearable device, the wearable sensor data together with one or more disease-specific alert settings to determine whether the user is exhibiting symptoms of a disease; instructing the user, with the wearable device when the analysis indicates that the user is exhibiting symptoms of a disease, to place the at least one microphone on a specific location on the user's body for obtaining audio data for auscultation for diagnosing whether the user has the disease.

Various embodiments described herein relate to a non-transitory machine-readable storage medium encoded with instructions for execution by wearable device worn by a user, the wearable device having a display and wearable sensors, the wearable sensors including at least one microphone, the medium including instructions for: monitoring, with the wearable device, wearable sensor data generated by the wearable sensors; analyzing, with the wearable device, the wearable sensor data together with one or more disease-specific alert settings to determine whether the user is exhibiting symptoms of a disease; instructing the user, with the wearable device when the analysis indicates that the user is exhibiting symptoms of a disease, to place the at least one microphone on a specific location on the user's body for obtaining audio data for auscultation for diagnosing whether the user has the disease.

Various embodiments described herein relate to a wearable device for diagnosing a disease including: a display; wearable sensors including at least one microphone; and a machine-readable storage medium for storing machine executable instructions designed and configured to cause the wearable device to: monitor wearable sensor data generated by said wearable sensors; analyze the wearable sensor data together with one or more disease-specific alert settings to determine whether the user is exhibiting symptoms of a disease; and instruct the user, when the analysis indicates that the user is exhibiting symptoms of a disease, to place the at least one microphone on a specific location on the user's body for obtaining audio data for auscultation for diagnosing whether the user has the disease.

Various embodiments additionally include displaying, on the wearable device display, a disease-selection user interface (UI) for displaying a plurality of diseases the wearable device may be configured to monitor for; receiving a user selection, via the disease-selection UI, of at least one disease for monitoring and diagnosis; and configuring the wearable device, based on the user selection, with the disease-specific alert settings for executing said analyzing.

Various embodiments additionally include transmitting the user selection from the wearable device to a network having a server alert database having a plurality of disease-specific alert settings corresponding to respective ones of the plurality of diseases; and receiving, from the server alert database, the disease-specific alert settings.

Various embodiments additionally include transmitting, with the wearable device, the audio data to a third party diagnostician; receiving, with the wearable device, a diagnosis message from the third party diagnostician; and displaying, on the wearable device display, the diagnosis message.

Various embodiments are disclosed wherein said instructing includes displaying, on the wearable device display, a user alert UI, the user alert UI having: at least one triggering data field for displaying the wearable sensor data that meets or exceeds the one or more disease-specific alert settings; and an alert message field for displaying an alert message for notifying the user of the disease the user is exhibiting symptoms of.

Various embodiments are disclosed wherein said instructing includes providing visual instructions on the display including a visual representation of a human body with an indicator for graphically showing the specific location of the body where the at least one microphone should be placed.

Various embodiments are disclosed wherein said instructing includes providing at least one of visual, audio, and haptic feedback with the wearable device for indicating when the at least one microphone is getting closer or getting farther away from the specific location on the user's body.

Various embodiments are disclosed wherein the wearable sensor data includes at least one of user respiration rate, user heart rate, user temperature, user blood pressure, user movement, user audio, user blood oxygen level, and user blood glucose level.

Various embodiments additionally include processing, with the wearable device, the wearable sensor data to generate processed sensor data, wherein said comparing further includes comparing the processed sensor data to the one or more disease-specific alert settings.

Various embodiments are disclosed wherein said processing includes processing the user audio to identify user disease symptom sounds.

Various embodiments are disclosed wherein said processing includes generating cumulative sensor data from the sensor data and the processed data.

Various embodiments are disclosed wherein said processing includes: selecting an algorithm of a plurality of audio processing algorithms based on the step of analyzing, wherein the selected algorithm is associated with at least one of the disease and the specific location of the user's body; and applying the selected algorithm to process the user audio.

BRIEF DESCRIPTION OF THE DRAWINGS

In order to better understand various example embodiments, reference is made to the accompanying drawings, wherein:

FIG. 4 shows an exemplary table of diseases that require auscultation by a health professional;

FIG. 5 shows an exemplary wearable device disease-selection graphical user interface (GUI);

FIG. 7 shows an exemplary server download database;

FIG. 10A shows an exemplary wearable device wearable sensor database;

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

Aspects of the present disclosure include an audio database for health systems and associated devices and methods that may utilize wearable devices that monitor wearable sensor readings for possible health issues and may prompt a user to place a microphone from the wearable device in a specific location on the user's body for recording an audio file that may be sent to a health professional for diagnosis. Such systems may provide a variety of benefits, including allowing users to avoid unnecessary visits to the doctor's office, and saving people the time, money, and anxiety of a medical office visit. Aspects may also be used by family or friends to help convince unwilling loved ones that they have a serious medical issue and need to see a doctor. Use of the systems and devices disclosed herein may also be encouraged by medical groups as a way to triage patients, thereby cutting down on unnecessary medical exams and prioritizing more immediate issues.

Figure 1:
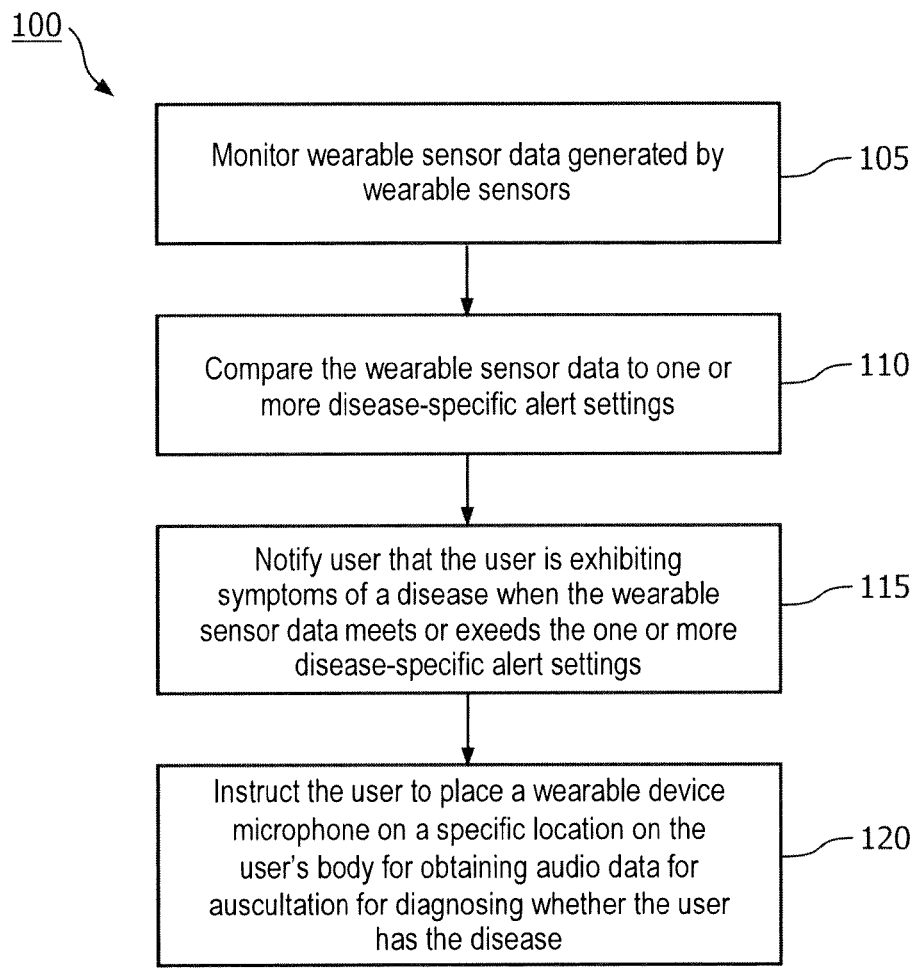
FIG. 1 shows an example method for diagnosing a disease in a user with a wearable device.

FIG. 1 illustrates an exemplary method 100 of diagnosing a disease in a user using systems and devices disclosed herein, including wearable devices configured to monitor wearable sensor data and notify a user when the wearable sensor data indicates the user is exhibiting symptoms of a disease. As used herein, the term "disease" may broadly refer to any disease, health issue, ailment, condition, or illness. In some embodiments, the disease may be of a type for which auscultation by a health professional is useful to diagnose the disease. Non-limiting examples of specific diseases that wearable devices made in accordance with the present disclosure may be configured to monitor for may include aerophagia, asthma, pertussis, pneumonia, chronic obstructive pulmonary disease, and sleep apnea. In other examples, wearable devices may be configured to monitor for any one of a variety of other diseases. In some embodiments, the wearable devices may include a display, and wearable sensors where the wearable sensors may include one or more microphones. The wearable sensors may also include any number of sensors known in the art for monitoring health data associated with a user. As a non-limiting example, the wearable sensors may include any number of a variety of sensors configured to generate a signal representative of one or more of respiration rate, user heart rate, user temperature, user blood pressure, user movement, user audio, user blood oxygen level, and user blood glucose level, as well as environmental data, such as environmental temperature, ambient noise, etc. As shown in FIG. 1, method 100 may include a step 105 of monitoring data from the wearable sensors and at step 110, comparing the wearable sensor data to one or more disease-specific alert settings. At step 115 the method may include notifying a user that the user is exhibiting symptoms of a disease when the wearable sensor data meets or exceeds the one or more disease-specific alert settings, and at step 120, the method may include instructing the user to place the at least one microphone on a specific location on the user's body for obtaining audio data for auscultation for diagnosing whether the user has the disease.

Figure 2:
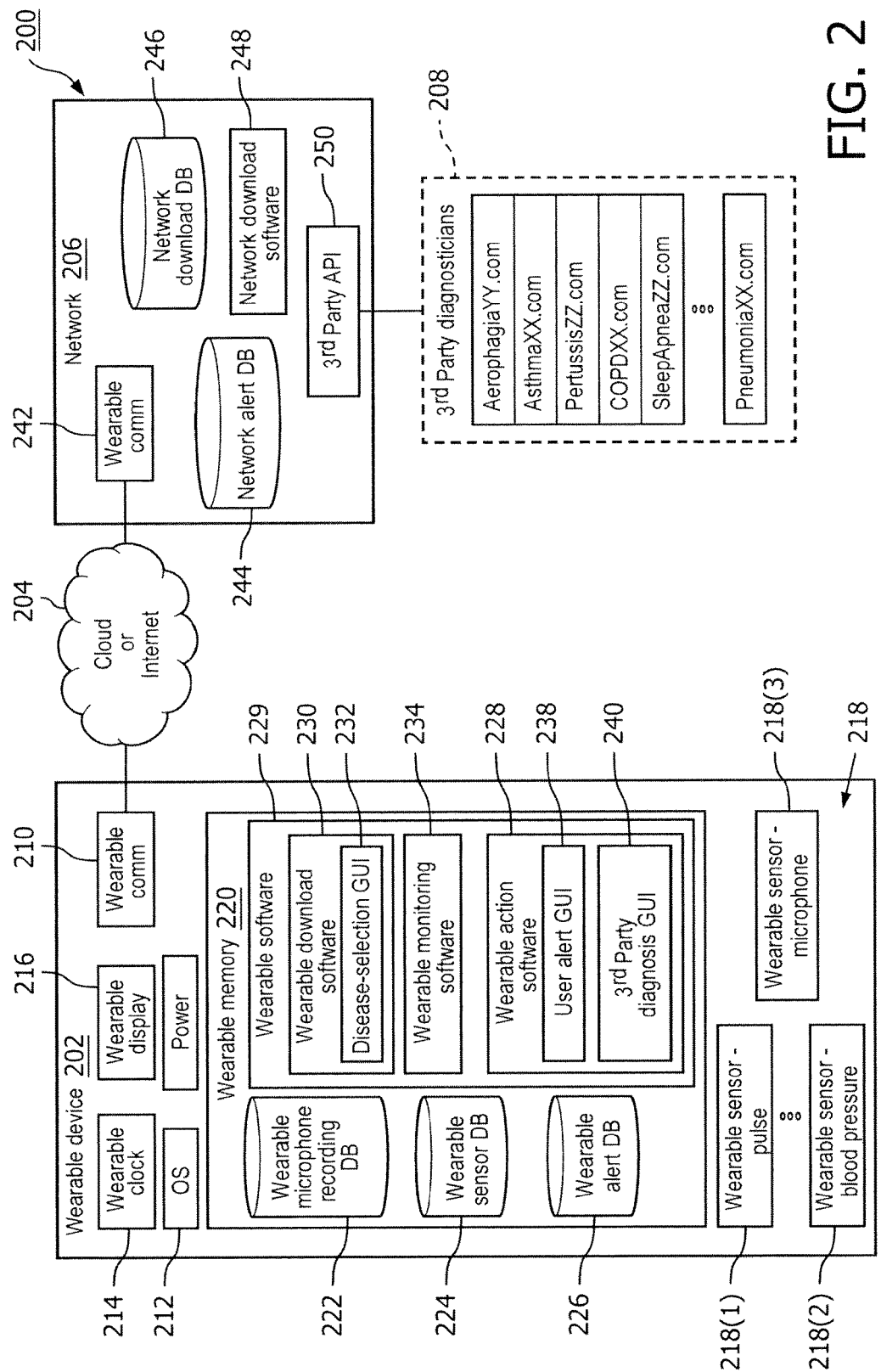
FIG. 2 shows an exemplary audio database for health system.

FIG. 2 illustrates an exemplary audio database for health system 200 for implementing aspects of the present disclosure. As shown, exemplary system 200 may include one or more wearable devices 202 (one shown for convenience) connected via a communication network 204 (e.g., a LAN, carrier network, software-defined network within one or more cloud computing architectures, or the Internet), to a server 206 that may in turn be connected to a plurality of third-party diagnosticians 208 for providing diagnostic analyses of health data, including audio files provided by wearable devices 202. As shown, each wearable device 202 may include a communications interface 210 for communicating with server 206 and diagnosticians 208 via, for example, the communication network 204 by any communications means, including WI-FI protocol, BLUETOOTH protocol, 4G LTE protocol, etc.

Each wearable device 202 may have an operating system ("OS") 212, a clock 214 and a display 216, e.g., touch display, and may also have a plurality of wearable sensors 218, such as any of the ones listed above, as well as a pulse sensor 218(1), a blood pressure sensor 218(2), a respiratory rate sensor (not shown), and one or more microphones 218(3), etc. It will be apparent that various alternative or additional sensors may be incorporated into the wearable device 202 or other wearable devices (not shown) that operate in conjunction with the wearable device 202. In some embodiments, the sensor devices may sense physiological parameters about the user. For example, the sensor devices 218 may include accelerometers, conductance sensors, optical sensors, temperature sensors, microphones, cameras, etc. These or other sensors may be useful for sensing, computing, estimating, or otherwise acquiring physiological parameters descriptive of the wearer such as, for example, steps taken, walking/running distance, standing hours, heart rate, respiratory rate, blood pressure, stress level, body temperature, calories burned, resting energy expenditure, active energy expenditure, height, weight, sleep metrics, etc. In some cases, the raw data obtained by sensors may constitute physiological parameters usable by other functionalities while, in other cases, the raw data may be processed (e.g., by the wearable device 202, the server 206, another device of the user, another server, etc.) to extract parameters. For example, color data obtained by an optical sensor may be processed over a time window to estimate a user's pulse.

Wearable device 202 may also include a memory 220 that, as illustrated, may store a variety of software programs and databases. The exemplary wearable device memory databases may include a wearable microphone recording database 222 for storing recorded audio data, a wearable sensor database 224 for storing data from sensors 218 other than microphone(s) 218(3), and an alert database 226 that may contain disease-specific alert settings for triggering the action software 228 (discussed below) to take an action. Such action may include, for example, notifying a user that the user is exhibiting symptoms of a specific disease requiring auscultation for diagnosis and instructing the user to use sensor microphone 218(3) to generate an audio file for further diagnosis.

Wearable device 202 may also include a variety of wearable software 229, including download software 230 and associated disease-selection graphical user interface (GUI) 232 for downloading specific disease-specific alert settings from server 206 for specific health diseases. For example, a user may wish to download disease-specific alert settings from server 206 related to a specific health issue he or she would like to monitor and possibly diagnose. In some examples, wearable device alert database 226 may already contain disease-specific alert settings for a plurality of diseases and disease-selection GUI 232 may be used to select one or more of the diseases for monitoring and possible diagnosis. Wearable memory 220 may also contain monitoring software 234 that may be used for comparing wearable sensor data to the disease-specific alert settings in alert database 226 to determine if the data meets or exceeds the one or more disease-specific alert settings. If so, monitoring software 234 may execute or cause to be executed action software 228 for performing actions prescribed by data in alert database 226 associated with the alerts that were triggered. Action software 228 may also include a user alert GUI 238 and a third-party diagnosis GUI 240. User alert GUI 238 may be used for displaying a message to the user identifying what has been triggered and next steps, including where the user needs to place microphone(s) 218(3) for taking additional readings. Third-party diagnosis GUI 240 may be used for receiving a diagnosis message from any of third-party diagnosticians 208. In some examples, one or more sound analysis software and algorithms (not shown) may be stored in wearable memory 220 and wearable device 202 may be configured to analyze audio data from microphone(s) 218(3) to both determine if the user is exhibiting symptoms of a disease, and/or to perform a preliminary diagnosis of additional audio data obtained by a user in response to the alert. For example, rather than send audio data to one of third-party diagnosticians 208 for auscultation, wearable device 202 may be configured with software (not shown) for analyzing audio data to diagnose a particular disease. In yet other examples, one or more algorithms may be executed for performing a preliminary diagnosis that may be transmitted to one of third-party diagnosticians 208 along with, in some examples, the audio data used to perform the diagnosis, for analysis.

Exemplary server 206 may include a communications module 242 for communicating with each wearable device 202, a server alert database 244 for storing disease-specific alert settings for various health diseases, a server download database 246 for storing a listing of health diseases along with corresponding identification of knowledgeable third-party diagnosticians 208, information on the one or more sensors required for diagnosing the disease, and a unique identifier for the corresponding server alert database 244 associated with a given health issue. The server download software 248 may be used to send server alert databases 244 (or portions thereof) to wearable devices 202. For example, server download software 248 may receive a request from the wearable device download software 230 for data associated with one or more health issues that the user wishes to download, and the server download software may find the matching server alert database(s) 244 for the one or more health issues, and send a copy of the database(s) to wearable device 202. In other embodiments, wearable device 202 may not receive a copy of alert databases 244 associated with a disease and may instead be configured to access the data residing on server 206. The third-party API 250 may be used for transmittal of information between network and third-party diagnosticians 208, including sending audio files from wearable devices 202 to diagnosticians 208 to listen and diagnose, and to receive diagnosis messages from the diagnosticians for sending to the wearable device. It will be apparent that, while the server 206 is illustrated as a single device, in some embodiments the various functionalities ascribed to the server 206 may be ascribed to multiple complementary or redundant devices (e.g., a network of devices or a group of virtual machines within a cloud computing environment).

While not illustrated, it will be apparent that the various devices 202, 206 in the example system 200 include hardware, such as one or more processors each, to carry out the functionalities described herein. As used herein, the term "processor" will be understood to encompass various hardware devices such as, for example, microprocessors, field-programmable gate arrays (FPGAs), application specific integrated circuits (ASICs), and other hardware devices capable of performing the various functions described herein as being performed by the wearable device 202, server 252, or other device. Further, the memory devices 220 may include various devices such as L1/L2/L3 cache, system memory, or storage devices. Further, while not shown, some of the components of the server (e.g., components 244, 246, 248, 250) will also be understood to be stored among one or more similar memory devices. As used herein, the term "non-transitory machine-readable storage medium" will be understood to refer to both volatile memory (e.g., SRAM and DRAM) and non-volatile memory (e.g., flash, magnetic, and optical memory) devices, but to exclude mere transitory signals. While various embodiments may be described herein with respect to software or instructions "performing" various functions, it will be understood that such functions will actually be performed by hardware devices such as a processor executing the software or instructions in question. In some embodiments, such as embodiments utilizing one or more ASICs, various functions described herein may be hardwired into the hardware operation; in such embodiments, the software or instructions corresponding to such functionality may be omitted.

Figure 3:
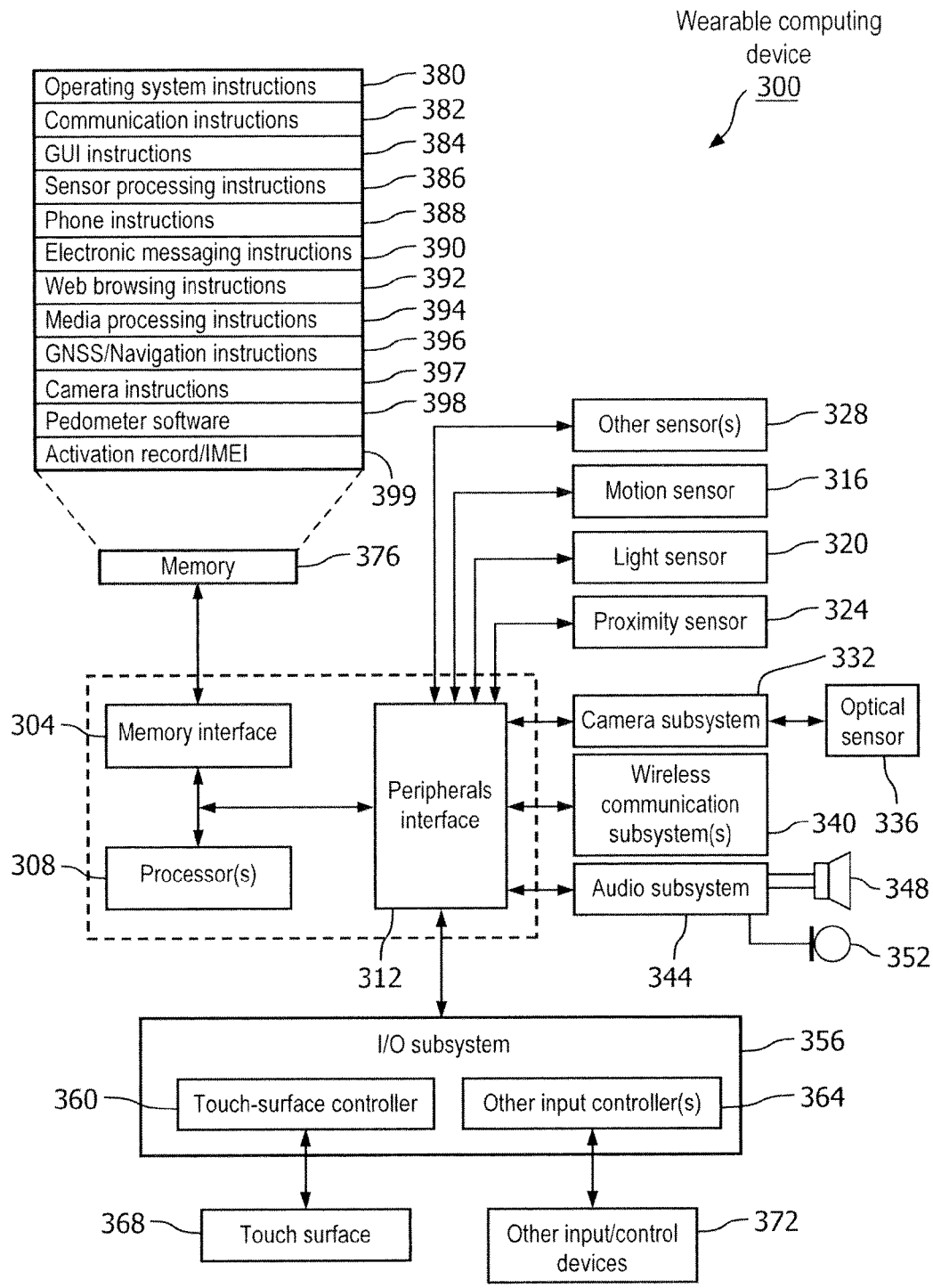
FIG. 3 is a block diagram of an exemplary architecture and functionality of a computing device that may be incorporated in a wearable device.

FIG. 3 is a block diagram of an example wearable computing device 300 that may be configured to implement any one or more of various features and/or processes of the present disclosure, such as the features and processes illustrated in other figures of this disclosure, as well as features and processes that would be apparent to those of ordinary skill in the art after reading this entire disclosure. As shown, computing device 300 may include a memory interface 304, one or more data processors, image processors and/or central processing units 308, and a peripherals interface 312. Memory interface 304, one or more processors 308, and/or peripherals interface 312 may be separate components or may be integrated in one or more integrated circuits. The various components in computing device 300 may be coupled by one or more communication buses or signal lines.

Sensors, devices, and subsystems may be coupled to peripherals interface 312 to facilitate one or more functionalities. For example, a motion sensor 316, a light sensor 320, and a proximity sensor 324 may be coupled to peripherals interface 312 to facilitate orientation, lighting, and/or proximity functions. In some examples, one or more of the motion, light, and proximity sensors may be used for providing instructions or feedback to a user for placing a wearable device microphone on the appropriate location of the user's body for obtaining audio data for auscultation. Other sensors 328 may also be connected to peripherals interface 312, such as a global navigation satellite system (GNSS) (e.g., GPS receiver), a temperature sensor, a biometric sensor, and/or one or more other sensing devices, to facilitate related functionalities.

A camera subsystem 332 and an optical sensor 336, e.g., a charged coupled device (CCD) or a complementary metal-oxide semiconductor (CMOS) optical sensor, may be utilized to facilitate camera functions, such as recording images and/or video. Camera subsystem 332 and optical sensor 336 may be used to collect images of a user to be used during authentication of a user, e.g., by performing facial recognition analysis, and may also be used to determine a location of the wearable device in location to a user's body for providing feedback to a user for locating a microphone on the appropriate location on a user's body.

Communication functions may be facilitated through one or more wireless communication subsystems 340, which may include radio frequency receivers and transmitters and/or optical (e.g., infrared) receivers and transmitters. The specific design and implementation of communication subsystem 340 may depend on the communication network(s) over which computing device 300 is intended to operate. For example, computing device 300 may include communication subsystems 340 designed to operate over a GSM network, a GPRS network, an EDGE network, a Wi-Fi™ or WiMax™ network, and/or a Bluetooth™ network. In particular, wireless communication subsystems 340 may include hosting protocols such that one or more devices 300 may be configured as a base station for other wireless devices.

An audio subsystem 344 may be coupled to a speaker 348 and a microphone 352 to facilitate voice-enabled functions, such as speaker recognition, voice replication, digital recording, and/or telephony functions. Audio subsystem 344 may be configured to facilitate processing voice commands, voice-printing, and voice authentication.

I/O subsystem 356 may include a touch-surface controller 360 and/or other input controller(s) 364. Touch-surface controller 360 may be coupled to a touch surface 368. Touch surface 368 and touch-surface controller 360 may, for example, detect contact and movement or a lack thereof using one or more of any of a plurality of touch sensitivity technologies, including but not limited to capacitive, resistive, infrared, and/or surface acoustic wave technologies, optionally as well as other proximity sensor arrays and/or other elements for determining one or more points of contact with touch surface 368.

Other input controller(s) 364 may be coupled to other input/control devices 372, such as one or more buttons, rocker switches, thumb-wheel, infrared port, USB port, and/or a pointer device such as a stylus. One or more related buttons or other controls (not shown) may include one or more sets of up/down buttons for volume and/or amplitude control of speaker 348 and/or microphone 352. Using the same or similar buttons or other controls, a user may activate a voice control, or voice command, module that enables the user to speak commands into microphone to cause device 300 to execute the spoken command. The user may customize functionality of one or more buttons or other controls. Touch surface 368 may, for example, also be used to implement virtual or soft buttons and/or a keyboard.

In some implementations, computing device 300 may present recorded audio and/or video files, such as MP3, AAC, and/or MPEG files. In some implementations, computing device 300 may include the functionality of an MP3 player, such as an iPod™. Computing device 300 may, therefore, include a 36-pin connector that is compatible with related iPod™ hardware. Other input/output and control devices may also be used.

As shown, memory interface 304 may be coupled to one or more types of memory 376. Memory 376 may include high-speed random access memory and/or non-volatile memory, such as one or more magnetic disk storage devices, one or more optical storage devices, and/or flash memory (e.g., NAND, NOR). Memory 376 may store an operating system 380, such as Darwin™ RTXC, LINUX, UNIX, OS X™, WINDOWS™, and/or an embedded operating system such as VxWorks. Operating system 380 may include instructions for handling basic system services and/or for performing hardware dependent tasks. In some implementations, operating system 380 may include a kernel (e.g., UNIX kernel). Further, in some implementations, operating system 380 may include instructions for performing voice authentication.

Memory 376 may also store communication instructions 382 to facilitate communicating with one or more additional devices, one or more computers, and/or one or more servers. Additionally or alternatively, memory 376 may include: graphical user interface instructions 384 to facilitate graphic user interface processing; sensor processing instructions 386 to facilitate sensor-related processing and functions; phone instructions 388 to facilitate phone-related processes and functions; electronic messaging instructions 390 to facilitate electronic-messaging related processes and functions; web browsing instructions 392 to facilitate web browsing-related processes and functions; media processing instructions 394 to facilitate media processing-related processes and functions; GNSS/Navigation instructions 396 to facilitate GNSS and navigation-related processes and instructions; and/or camera instructions 397 to facilitate camera-related processes and functions. Memory 376 may store other software instructions 398 to facilitate other processes and functions. For example, other software instructions 398 may include instructions for counting steps the user takes when device 300 is worn.

Memory 376 may also store other software instructions (not shown), such as web video instructions to facilitate web video-related processes and functions and/or web shopping instructions to facilitate web shopping-related processes and functions. In some implementations, media processing instructions 394 may be divided into audio processing instructions and video processing instructions to facilitate audio processing-related processes and functions and video processing-related processes and functions, respectively. An activation record and International Mobile Equipment Identity (IMEI) 399 or similar hardware identifier may also be stored in memory 376.

Each of the above identified instructions and applications may correspond to a set of instructions for performing one or more functions described herein. These instructions need not necessarily be implemented as separate software programs, procedures, or modules. Memory 376 may include additional instructions or fewer instructions. Further, various functions of computing device 300 may be implemented in hardware and/or in software, including in one or more signal processing and/or application specific integrated circuits.

FIG. 4 shows an exemplary table 400 of diseases that require or benefit from auscultation by a health professional to diagnose the disease that systems and devices of the present disclosure may be used to detect and diagnose. The illustrated table includes exemplary diseases 404 listed along the left-most column and the typical symptoms 408 associated with the diseases along the top row. The cells at the intersection of the disease and an associated symptom show examples of instructions 410 that may be provided to a user for obtaining auscultation information required to diagnose the disease. Thus, as will be described more below, a table such as the table in FIG. 4 may be used to generate alert databases for specific diseases that may include disease-specific alert settings for triggering an alert for notifying a user that the user is exhibiting symptoms of a particular disease. FIG. 4 also shows example instructions that may be displayed to a user, for example, on a wearable device display for instructing the user to use a microphone on the wearable device to obtain audio data from a specific location on the user's body that may be sent to a health professional for diagnosis. For example, to monitor a user to determine if the user has asthma, a wearable device may be configured to use one or more audio manipulation and processing algorithms for processing microphone wearable sensor data being acquired by the wearable device to isolate user audio data from ambient sounds and determine if the user has a recurrent cough or wheezing. The device may also be configured to record instances of detected coughing or wheezing and calculate a cumulative data value for tracking the number of instances of the occurrence over a predetermined period of time, which may be compared to one or more disease-specific alert settings. For example, whether the detected coughing or wheezing has occurred more than three times per day for more than three days. If the device detects such recurrent coughing or wheezing, the user may be notified of the detection and instructed to place the microphone on the user's chest to listen to the lungs for an airflow obstruction. As will be appreciated, such functionality may provide a variety of benefits. For example, a user may not think a periodic cough is of concern and may therefore disregard it and delay proper medical treatment, whereas the device may be configured to consistently monitor and process user audio data to monitor for key indications of symptoms of a disease and notify the user when such otherwise undetected conditions are detected by the device.

After recording the audio file, the audio file may then be transmitted to a health professional for diagnosis and a diagnosis may be returned to the user, telling the user that he or she most likely doesn't have asthma, and does not need to waste his or her time going to the doctor, or that he or she may in fact have asthma and should seek further medical attention. As discussed above, in some embodiments, the wearable device may have one or more algorithms for analyzing the additional audio data to provide a preliminary diagnosis, which may or may not be sent to a third-party diagnostician. For example, each algorithm may be associated with a disease, group of diseases, microphone placement/body part, or group of placements/body parts. Upon advising the user to place the microphone at a particular location, the wearable device may select and execute an algorithm associated with the advised placement or suspected disease. Diagnoses for the other diseases illustrated in FIG. 4 as well as any other of a number of diseases may similarly be performed. As will be discussed more below, some disease-specific alert settings for some diseases may involve the monitoring of two or more wearable sensors that all must be triggered before the user receives an alert notification with instructions to record audio data.

FIG. 5 shows an exemplary wearable device disease-selection GUI 232 for allowing a user to choose a health issue 502 that they want to download to wearable device 202 for monitoring and diagnosis by a third-party diagnostician 504 and/or wearable device 202. As shown, disease-selection GUI 232 may be configured to display health issues 502 available in server download database 246 and/or locally available on wearable device 202, and may include main window 506 for displaying the disease along with, in some examples, the third-party diagnostician that would be diagnosing the wearable sensor data including audio files for diagnosing the condition and sensors used 508 for alert and diagnosis. In some cases, GUI 232 may display alternatives for a given disease for the user to select from. For example, more than one third-party diagnostician 504 may be available for diagnosing a given disease, and different disease detection programs may use different sensors for detection. In some examples, disease-selection GUI 232 may be provided by a medical group or insurance network and may indicate whether a particular third-party diagnostician 504 is in-network or out of network, and may provide additional information on third-party diagnostician 504, such as user ratings and the diagnostician's qualifications and certifications. In some embodiments, disease-selection GUI 232 may be configured to notify the user when the user has selected a disease program that requires a sensor the wearable device does not have, for example, in cases where the network is configured to communicate with a variety of different types of wearable devices having different types of sensors. As shown, the window may have a scroll bar 510 for scrolling through a long list of diseases, and as will be appreciated, server download database 246 may have a large number of entries to choose from. Wearable display 216 may be a touch display, allowing a user to select the disease for download by touching the screen. GUI 232 may also include a search window 512 for typing in search terms for a disease and may have a virtual keyboard 514 for entering the search terms. The user may download selected files by touching the download button 516 and close GUI 232 by touching the close button 518.

Figure 6A:
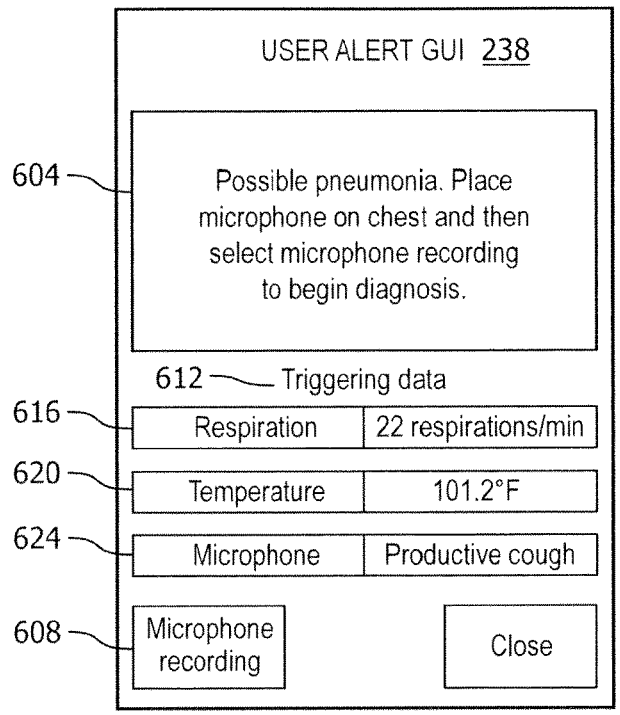
FIG. 6A shows an exemplary user alert GUI.
Figure 6B:
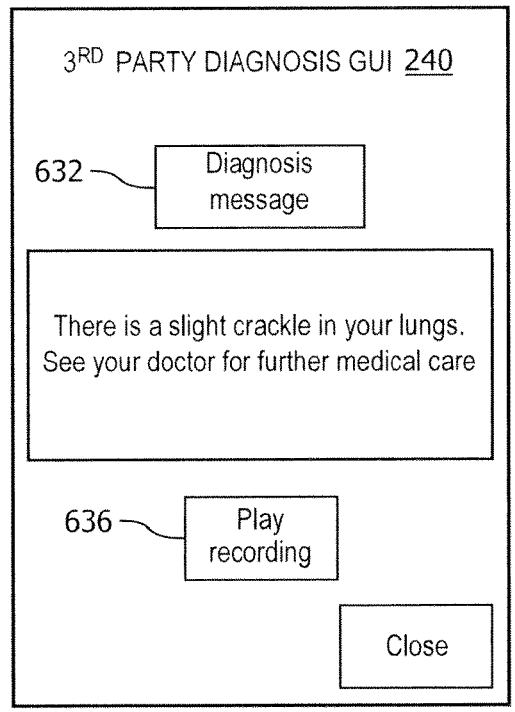
FIG. 6B shows an exemplary third-party diagnosis GUI.

FIGS. 6A and 6B show exemplary user alert and third-party diagnosis GUIs. The user alert GUI 238 (FIG. 6A) may be displayed when the monitoring software determines wearable sensor data meets or exceeds one or more disease-specific alert settings and may be configured to display a message 604 to the user to alert the user to a possible disease they might have and provide instructions for obtaining audio data for further analysis. In the example shown, the message is, "Possible Pneumonia; place microphone on chest and then select Microphone Recording to begin diagnosis." The illustrated GUI may also have a microphone recording button 608 to begin taking audio data and may also notify the action software that the microphone is in place and audio recording is beginning. As discussed above, the wearable device 202 may also be configured to provide additional instructions or feedback for instructing the user on the proper location of the user's body for locating the microphone. For example, visual instructions may be included on wearable device display 216 which may include a visual representation of a human body, such as a simple cartoon of an outline of a person, with an indicator for graphically showing the specific location of the body where the at least one microphone should be placed, such as a star or asterisk on the location of the cartoon corresponding to the specific location. In other examples, one or more of the sensors and algorithms discussed above may be used to determine a location of a microphone and/or wearable device relative to a user's body and providing visual, audio, and/or haptic feedback to the user indicating when the at least one microphone is getting closer or getting farther away from the specific location on the user's body. Examples of feedback may include colored LEDs that transition along a spectrum of colors such as from green to yellow to red as the device gets closer or further away, or audio and/or haptic feedback wherein one or more of the magnitude and/or frequency of the signal may vary according to proximity to the desired location. User Alert GUI 238 may also display the triggering data that triggered the alert. In the illustrated example, the triggering data includes a data type and an associated value, and the triggering data display may be configured to dynamically change the number of trigger data type fields depending on the number of sensor readings associated with the particular alert. In the example shown, the pneumonia alert is based on three different data types including respiration rate 616, temperature 620, and microphone 624. The illustrated User Alert GUI 238 also includes example trigger data values that may exceed the thresholds for a pneumonia alert, including high respiration rate and temperature and detection of a productive cough (e.g., by isolating sound emitted by the wearer, extracting various features such as duration, amplitude, frequencies, etc., and applying a model trained using a machine learning approach such as logistic regression).

FIG. 6B shows an example of the third-party diagnosis GUI 240, which may display a diagnosis message 632 from, for example, a third-party diagnostician. In this example, the message is, "There is a slight crackle in your lungs; see your doctor for further medical care," indicating a third-party diagnostician listened to the audio recording from the user's microphone and heard what he or she thinks is a slight crackle in the lungs, which is a sign for pneumonia. Third-party diagnosis GUI 240 may also include a play recording button 636 for allowing a user to play the recording so they can listen to the audio that they recorded and that the diagnosis is based on. The user may also be able to play the recording to a physician so the physician can hear the audio that gave rise to the diagnosis. Example embodiments may also include a variety of other communication techniques, including providing audio and video capability for live and pre-recorded communication between the user and the third-party diagnostician.

FIG. 7 shows an example table 700 illustrating server download database 246 (FIG. 2). In the illustrated example, the data format is substantially the same as the data displayed in the wearable device disease-selection GUI 232 (FIG. 5) because, as described above, it may be the source of the data displayed on the disease-selection GUI. As shown, server download database 246 may include a listing of available health issues 704 for download, third-party diagnostician(s) 708 associated with the health issue, and sensors used 712 for alert and diagnosis. In the example shown, third-party diagnostician field 708 may contain a unique URL for transmitting audio files to the diagnostician. Unlike disease-selection GUI 500 discussed above, server download database 246 may also include a server alert database column 714 or other database index for linking the server download database with specific alert databases. In the illustrated example, the index or linking column may include a unique identifier indicating the specific alert database associated with a given disease. In the illustrated example, the identifier is simply the name of the disease, however, as will be appreciated, other identifiers may be used and any one of a variety of conceptual schema known in the database art may be used for logically storing information associated with the disease-specific alert settings and other information.

Figure 8:
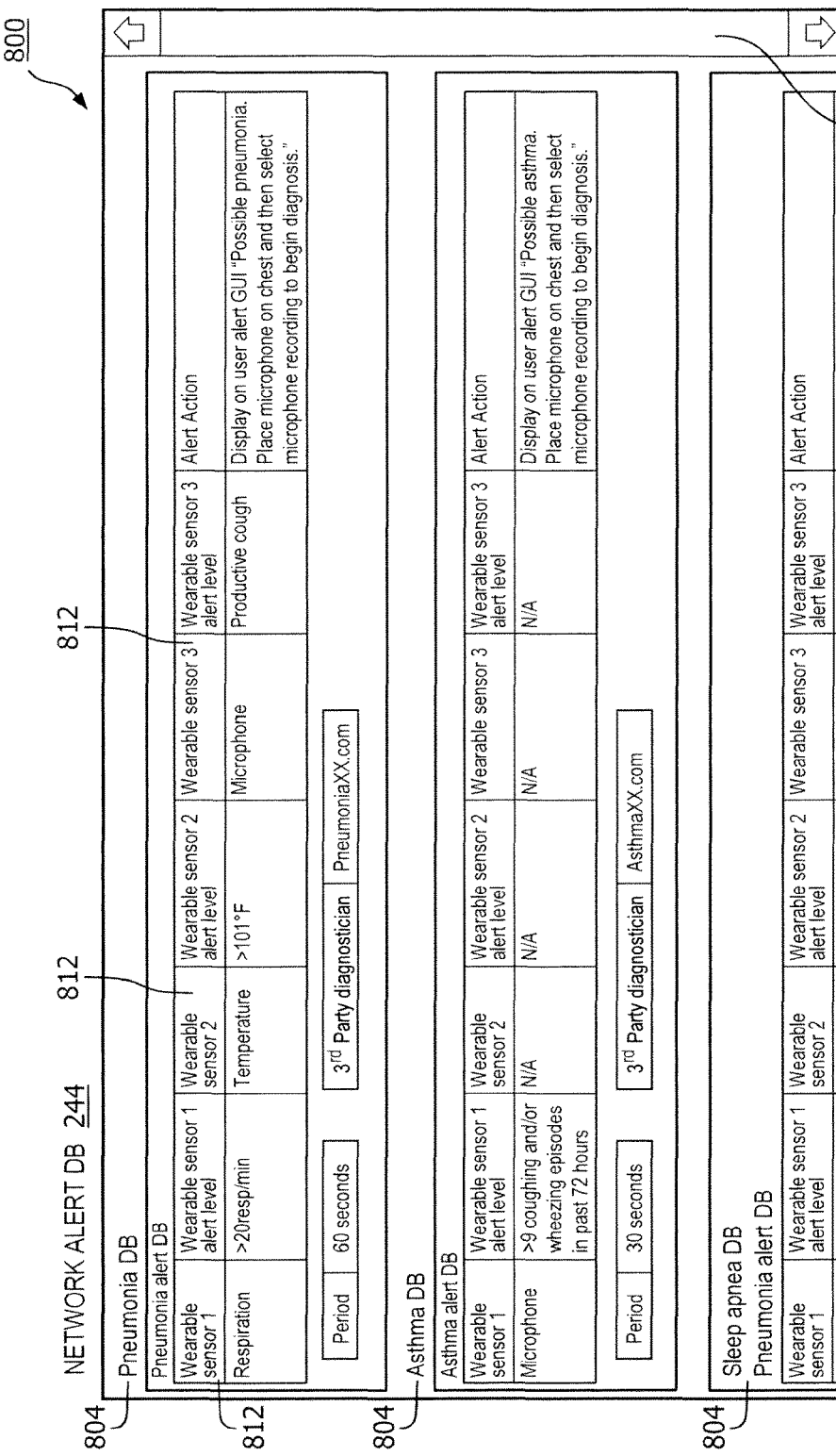
FIG. 8 shows an exemplary server alert database.
Figure 9:
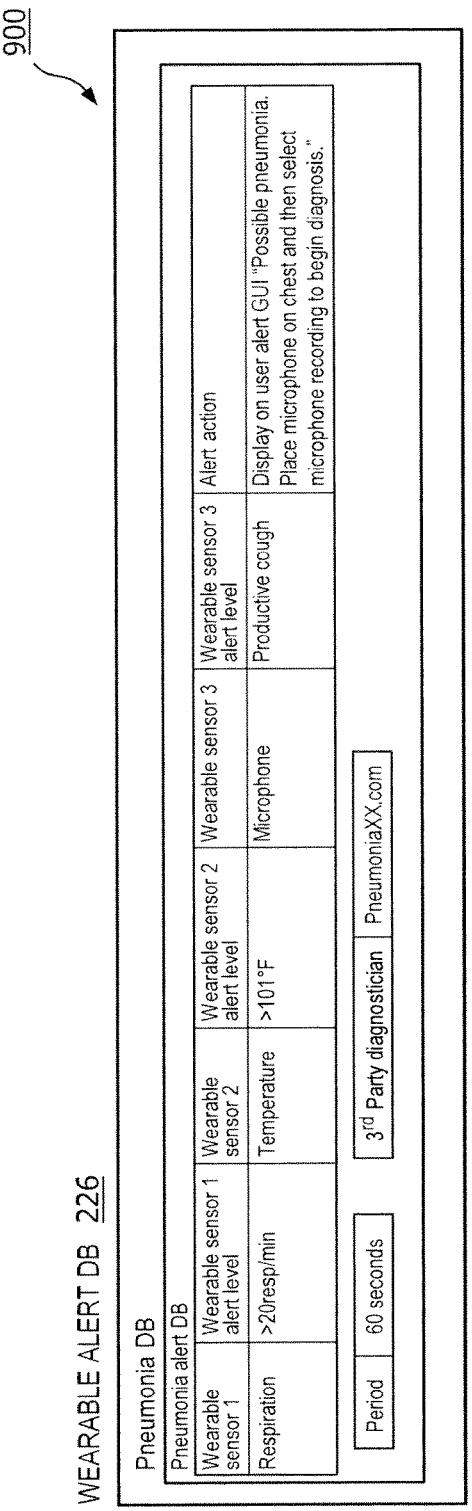
FIG. 9 shows an exemplary wearable device alert database.

FIG. 8 shows an example table 800 for server alert database 244. As shown, server alert database 244 may include a plurality of databases 804 associated with the listing of diseases in server download database 246. FIG. 8 includes a scroll bar 808 on the right side to conceptually illustrate the database may include any number of disease-specific alert databases with disease-specific alert settings, however, this is merely for illustration purposes. As shown, the disease-specific alert settings in each disease alert database may include information on the combination of wearable sensor data type and wearable sensor data values required for triggering an alert for a given disease. For example, the pneumonia database includes three wearable sensor data types 812 (respiration, temperature, and microphone) and associated threshold levels. In the illustrated example, to trigger the alert, all three thresholds must be exceeded at the same time. The pneumonia database may also include the alert message that may be displayed on wearable device alert GUI 238 when an alert is triggered. As shown, the disease alert databases may also include a microphone duration value specifying the duration of audio needed for the alert and may also include a third-party diagnostician field providing the contact information for the third-party diagnostician. FIG. 9 shows an example structure 900 for wearable device alert database 226 that, as described above, may be configured to receive one or more of the disease-specific alert databases from server alert database 244. In the illustrated example, wearable alert database 226 includes the pneumonia alert database which has been downloaded from server alert database 244 described immediately above (FIG. 8).

Figures 10B, 11:
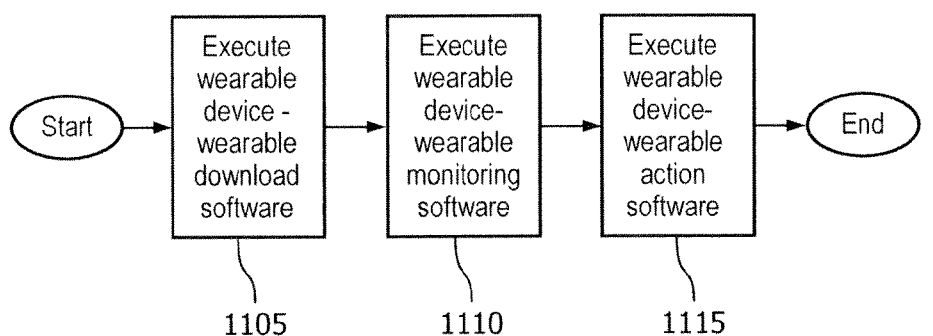
FIG. 10B shows an exemplary wearable device microphone database.
FIG. 11 shows an exemplary functionality for a wearable device wearable software.

FIGS. 10A and 10B show examples of wearable device sensor database 224 and wearable microphone recording database 222. As shown in FIG. 10A, wearable sensor database 224 may store data from all of the wearable device sensors, which in the illustrated example, include the date and time, pulse rate, blood pressure, microphone, respiration, temperature, and cumulative data from the microphone(s) relating to coughing and wheezing over a predetermined amount of time. As will be appreciated, any number of different sensor types may be included. In the illustrated example, the data is obtained every twenty minutes, however, any time interval may be used. Also as shown, wearable device 202 may be configured to process raw wearable sensor data for storing additional data in wearable sensor database 224. For example, wearable device 202 may include software for analyzing microphone data to determine if the recorded sounds represent a productive cough, or other health-related sounds. Wearable device 202 may also include software for processing the data, to calculate cumulative data values, such as the cough/wheeze in the past period of time. FIG. 10B shows an example of wearable device microphone database 222 which may be used for storing audio data in response to instructions from the action software for the user to place a microphone on a certain part of his or her body, and the audio file may begin to be recorded in the recording database when the user selects the microphone recording button in the alert GUI for recording an audio file for further diagnosis by a third-party diagnostician.

FIG. 11 shows example functionality 1100 for the wearable device wearable software, which may include at step 1105 executing wearable device download software 230 to allow a user to select a health issue or disease he or she wants to monitor and then download from server alert database 244, disease-specific alert settings specific to the disease the user selected. The software may also, at step 1110, execute wearable device monitoring software 234 for comparing the wearable sensor data stored in wearable sensor database 224 to disease-specific alert settings in wearable alert database 226 to determine if the data meets or exceeds the settings. At step 1110 wearable monitoring software 234 may continue to monitor until an alert is triggered, and when that occurs, the wearable software may execute the wearable action software 228, which may display user alert GUI 238, prompt the user to place the microphone on the appropriate location on his or her body to take an audio recording, and then send the audio recording to a third-party diagnostician, who may then send back a diagnosis message to the user on the wearable device.

Figure 12:
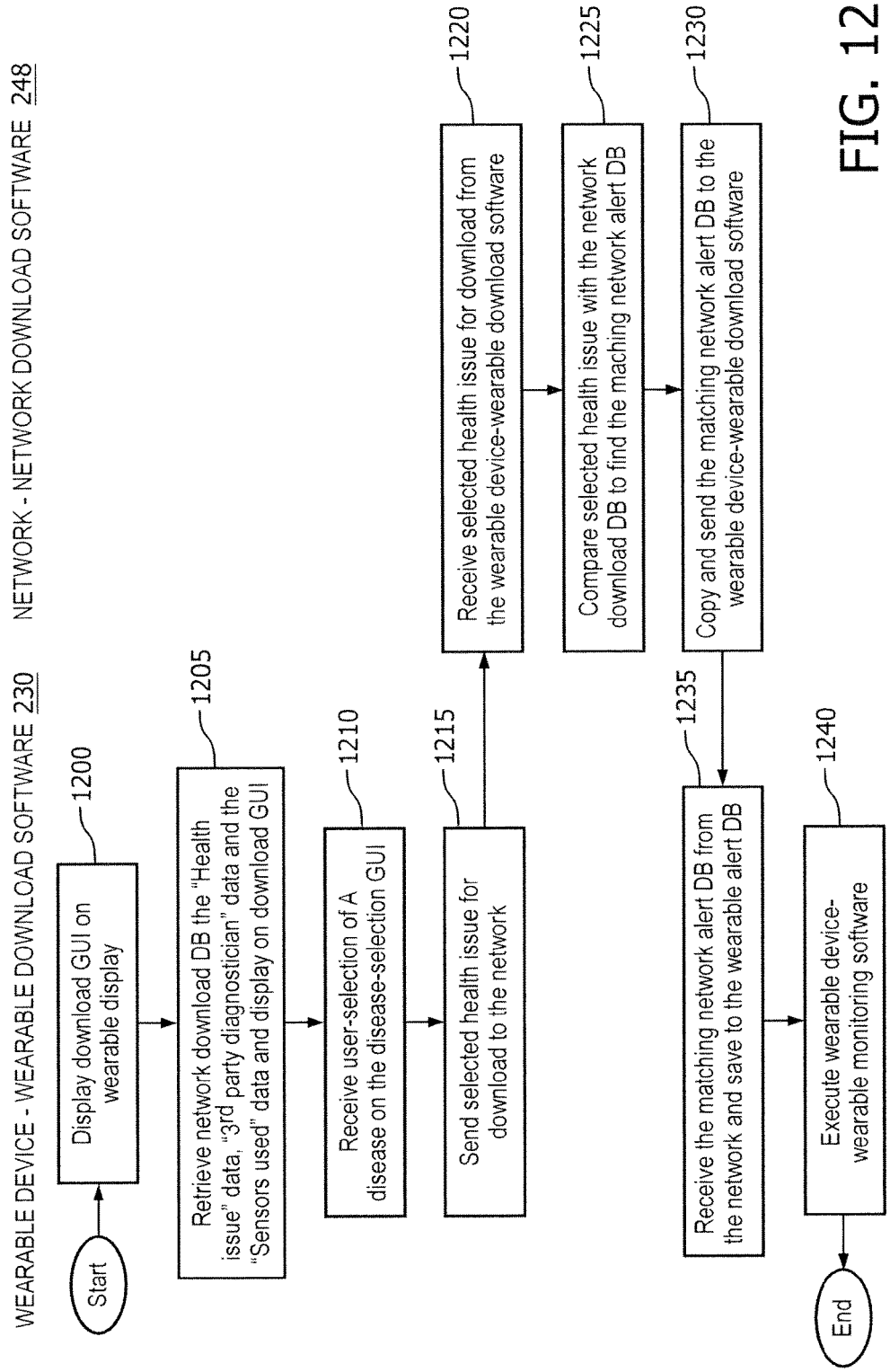
FIG. 12 shows exemplary functionality for a wearable device download software and a server download software.

FIG. 12 shows exemplary functionality for wearable device download software 230 and server download software 248 and exemplary interaction between the two. As shown, wearable device download software 230 may, at step 1200, display the disease-selection GUI on the device display and at step 1205, retrieve from the server download database the health disease programs available for download. The data may include health issue data, third-party diagnostician data, and required wearable sensor types. At step 1210 the program may then receive a selection from the user of a health issue displayed in the disease-selection GUI, for example, via selection of the Select button of the disease-selection GUI, and at step 1215 the program may then send a request for the user-selected health issue for download to the device. Server download software 248 may receive the request for the user-selected health issue for download from wearable device 202 at step 1220 and at step 1225 compare the selected health issue with information in server download database 246 to find the matching server alert database 244. At step 1230 the selected alert database is copied and sent to the wearable device 202. At step 1235 wearable device download software 230 may receive the uploaded server alert database 244 and save the alert database to wearable device alert database 226, and may then, at step 1240, execute the wearable device monitoring software 234.

Figure 13:
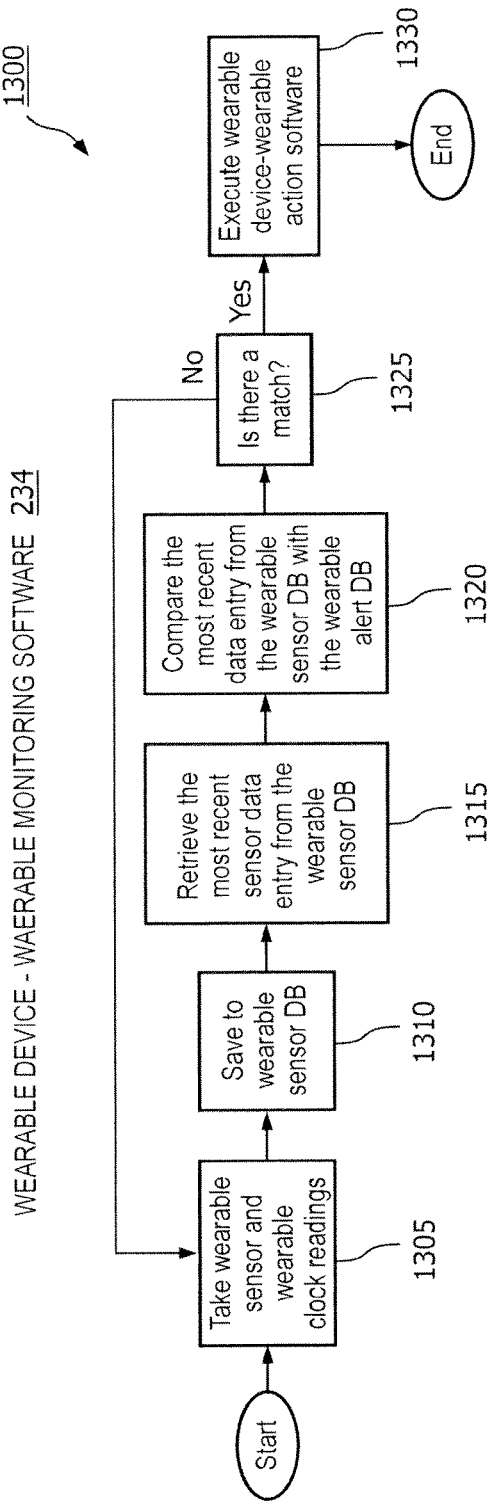
FIG. 13 shows exemplary functionality for a wearable device monitoring software.

FIG. 13 shows exemplary functionality 1300 for wearable device monitoring software 234. As shown at step 1305, the software may be configured to take wearable sensor and wearable clock readings and, at step 1310 save the readings to wearable sensor database 224. At step 1315, wearable monitoring software 234 may also retrieve or otherwise access the most recent wearable sensor data from wearable sensor database 224, and at step 1320, compare the most recent data (or physiological parameters based on recently obtained data, which will be understood to also constitute "wearable sensor data") with the wearable alert database to determine if there is a match (step 1325) or if the sensor data exceeds the disease-specific alert setting thresholds. If there is not a match, that is an indication that the disease the user has selected is not present and the program may loop back to step 1330 taking wearable sensor and wearable clock readings and performing the comparison, and once there is a match, wearable monitoring software 234 may execute or cause to be executed wearable device wearable action software 228 at step 1330.

It will be apparent that various alternatives to the rules and thresholds-based matching for step 1320 described above may be used in some embodiments. For example, in some embodiments, the alert settings may include values for a trained model (e.g., trained on a baseline data set using a machine learning approach such as, for example logistic regression) may be applied to one or more physiological parameters (sensed or extracted) to determine whether a given disease is suspected or whether the microphone should be placed at a given position. In such an embodiments, each disease or microphone position may be associated with a separate trained model. In some embodiments, one or more of these models may be further trained after delivery to the user by creating additional training examples based on actual interactions with the user and subsequently retraining the models using a machine learning algorithms. For example, where a model suggests placing the microphone on throat to detect aerophagia, but the gathered audio indicates (e.g., through application of an aerophagia analysis algorithm) that the user does not exhibit aerophagia, a new training example consisting of the parameters that were input into the model and a negative aerophagia label may be stored for later user. In various embodiments, the trained model may output a confidence level (e.g., between 0 and 1) which is then compared to a threshold (e.g., 0.5) to determine whether to output the microphone placement instruction. In some embodiments, this threshold may be manually set or otherwise based on input from the user.

Figure 14:
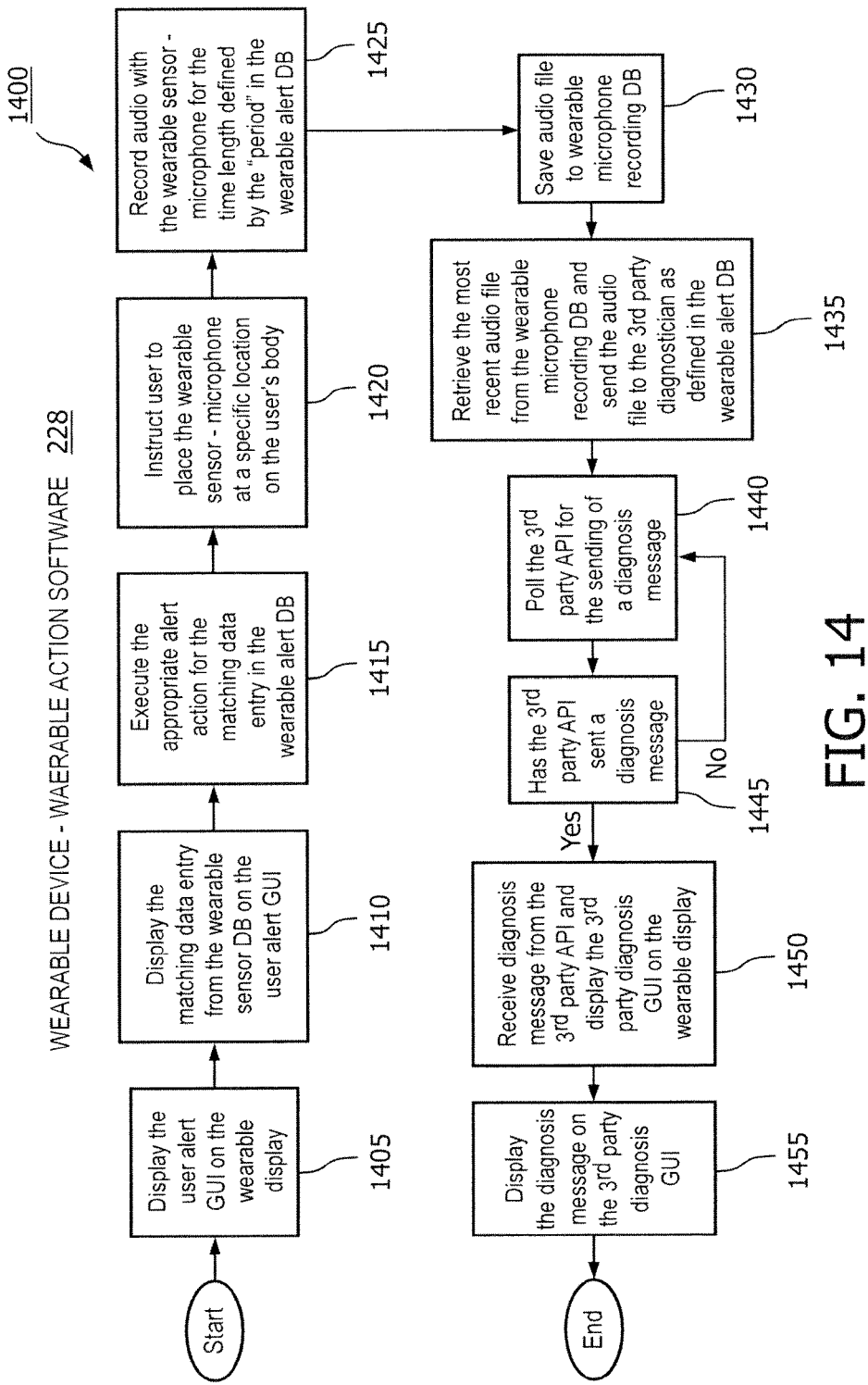
FIG. 14 shows exemplary functionality for a wearable device action software.

FIG. 14 shows example functionality 1400 for the wearable action software 228, which, at step 1405, may include displaying user alert GUI 238 on wearable display 216, and at step 1410 displaying the matching data entry from wearable sensor database 224 in user alert GUI 238 that triggered the alert. At step 1415, action software may also execute the appropriate alert message and, at step 1420 provide instructions for the matching data entry in wearable alert database 226, which may include a message for display on user alert GUI 238 that informs the user of the alert condition and the disease that has been detected. As described above, the message may also instruct the user to place the microphone on a specific location on the user's body for taking an audio recording. In one example, in response to the user's selection of the select microphone recording button on user alert GUI 238, or otherwise activation of the microphone, wearable action software 228 may then, at step 1425, record audio with the one or more wearable sensor microphones 218(3) for the length of time specified in the period field of wearable alert database 226. At step 1430, the file may then be saved to wearable microphone recording database 222 and at step 1435, sent to the third-party diagnostician, as defined in wearable alert database 226, for analysis. At step 1440 wearable action software 228 may also be configured to poll the third-party API for the receipt of the diagnosis message and at step 1445, may periodically or continuously poll the API until the diagnosis message is received. Once the diagnosis message is received at wearable device 220, at step 1450, action software 228 may display the message 1455 on third-party diagnosis GUI 240 on wearable display 216 for review by the user so the user can see what the third-party diagnostician thinks the user has.

Figure 15:
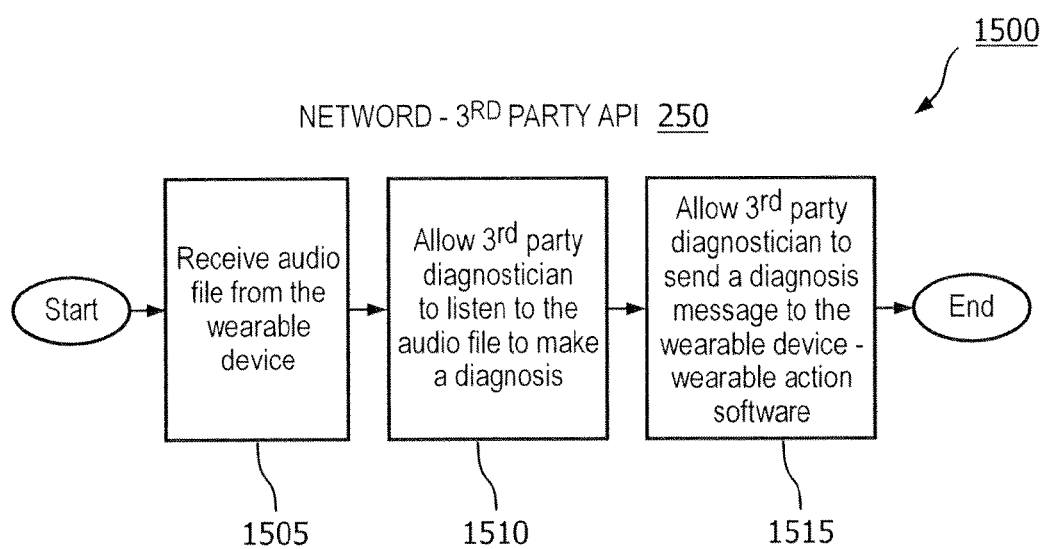
FIG. 15 shows exemplary functionality for a network third-party Application Program Interface ("API")

FIG. 15 shows exemplary functionality 1500 for network third-party API 250, which may, at step 1505 include receiving an audio file from wearable device 202, transmitting or otherwise allowing the third-party diagnostician to listen to the audio file and to make a diagnosis at step 1510, and receiving a diagnosis message from the third-party diagnostician to send to wearable device 202 for display on third-party diagnosis GUI 240 at step 1515. As will be appreciated, a variety of communication interfaces may be used with, or instead of, an API to perform one or more of these functions.

Thus, systems, devices and methods disclosed herein may be used for providing a wearable health system having an audio database for health. In some embodiments, the method may include providing a wearable device and network, such as a wearable device and network made in accordance with the present disclosure, and executing software on the wearable device for obtaining a user-selected one or more disease-specific alert database(s) from the network, using wearable device software to store and monitor wearable sensor data and compare the wearable sensor data to the downloaded alert database to monitor for symptoms of the user-selected disease, to display an alert to the user with an alert GUI and provide instructions for the user to place the device microphone(s) at a specific location on the user's body, to record audio data and to send the audio data to a third party diagnostician for diagnosis, and to receive a diagnosis from the diagnostician for display to the user on a third party diagnosis GUI. One or more additions or variations may be implemented as desired according to the various examples disclosed herein.

Any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 16:
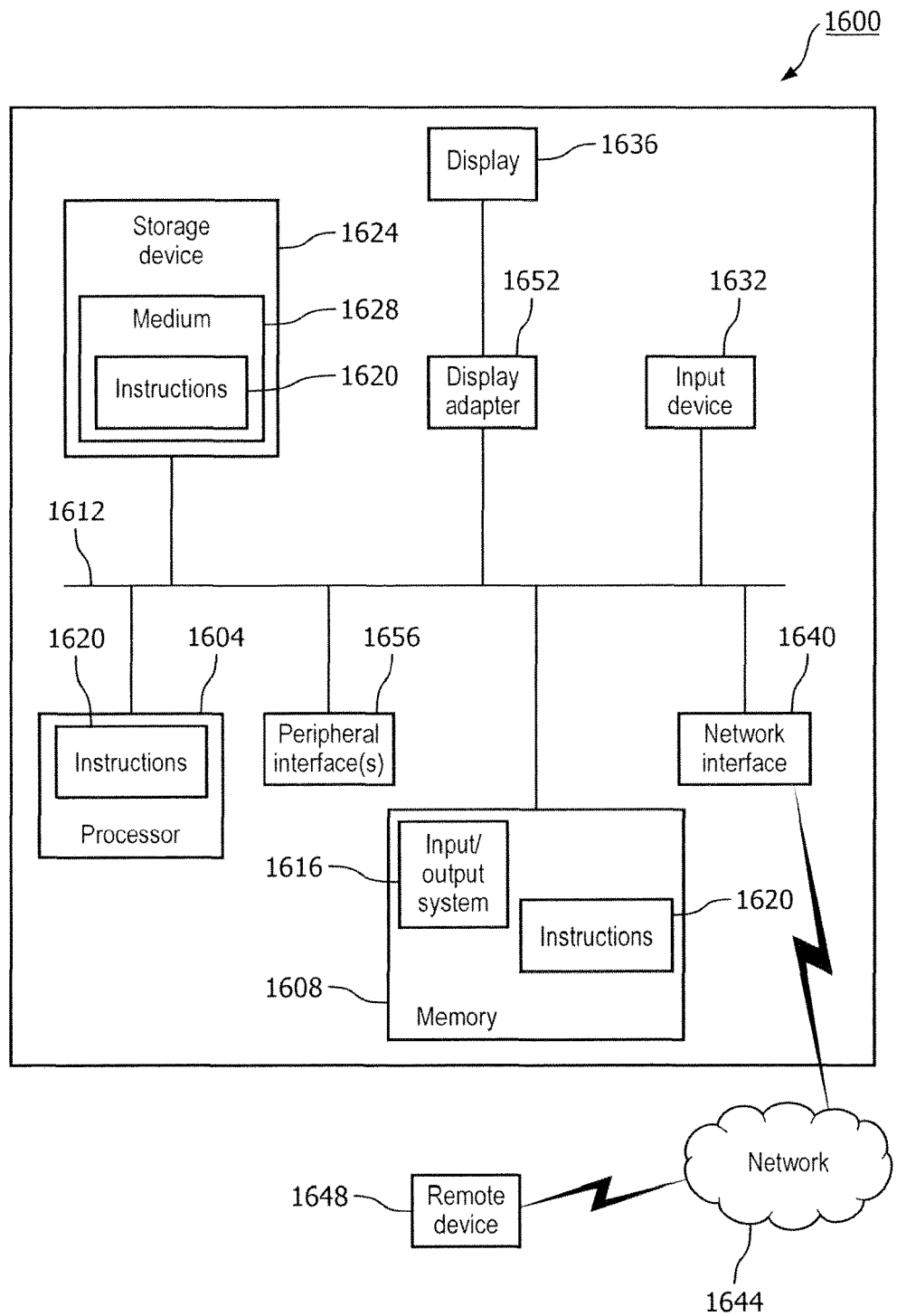
FIG. 16 is a block diagram of a computing system that can be used to implement any one or more of the methodologies disclosed herein and any one or more portions thereof.

FIG. 16 shows a diagrammatic representation of one embodiment of a computing device in the exemplary form of a computer system 1600 within which a set of instructions for causing a control system, such as the audio database for health system of FIG. 2, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1600 includes a processor 1604 and a memory 1608 that communicate with each other, and with other components, via a bus 1612. Bus 1612 may include any of several types of bus structures including, but not limited to, a memory bus, a memory controller, a peripheral bus, a local bus, and any combinations thereof, using any of a variety of bus architectures.

Memory 1608 may include various components (e.g., machine-readable media) including, but not limited to, a random access memory component, a read only component, and any combinations thereof. In one example, a basic input/output system 1616 (BIOS), including basic routines that help to transfer information between elements within computer system 1600, such as during start-up, may be stored in memory 1608. Memory 1608 may also include (e.g., stored on one or more machine-readable media) instructions (e.g., software) 1620 embodying any one or more of the aspects and/or methodologies of the present disclosure. In another example, memory 1608 may further include any number of program modules including, but not limited to, an operating system, one or more application programs, other program modules, program data, and any combinations thereof.

Computer system 1600 may also include a storage device 1624. Examples of a storage device (e.g., storage device 1624) include, but are not limited to, a hard disk drive, a magnetic disk drive, an optical disc drive in combination with an optical medium, a solid-state memory device, and any combinations thereof. Storage device 1624 may be connected to bus 1612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1624 (or one or more components thereof) may be removably interfaced with computer system 1600 (e.g., via an external port connector (not shown)). Particularly, storage device 1624 and an associated machine-readable medium 1628 may provide nonvolatile and/or volatile storage of machine-readable instructions, data structures, program modules, and/or other data for computer system 1600. In one example, software 1620 may reside, completely or partially, within machine-readable medium 1628. In another example, software 1620 may reside, completely or partially, within processor 1604.

Computer system 1600 may also include an input device 1632. In one example, a user of computer system 1600 may enter commands and/or other information into computer system 1600 via input device 1632. Examples of an input device 1632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1632 may be interfaced to bus 1612 via any of a variety of interfaces (not shown) including, but not limited to, a serial interface, a parallel interface, a game port, a USB interface, a FIREWIRE interface, a direct interface to bus 1612, and any combinations thereof. Input device 1632 may include a touch screen interface that may be a part of or separate from display 1636, discussed further below. Input device 1632 may be utilized as a user selection device for selecting one or more graphical representations in a graphical interface as described above.

A user may also input commands and/or other information to computer system 1600 via storage device 1624 (e.g., a removable disk drive, a flash drive, etc.) and/or network interface device 1640. A network interface device, such as network interface device 1640, may be utilized for connecting computer system 1600 to one or more of a variety of networks, such as network 1644, and one or more remote devices 1648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1644, may employ a wired and/or a wireless mode of communication. In general, any network topology may be used. Information (e.g., data, software 1620, etc.) may be communicated to and/or from computer system 1600 via network interface device 1640.

Computer system 1600 may further include a video display adapter 1652 for communicating a displayable image to a display device, such as display device 1636. Examples of a display device include, but are not limited to, a liquid crystal display (LCD), a cathode ray tube (CRT), a plasma display, a light emitting diode (LED) display, and any combinations thereof. Display adapter 1652 and display device 1636 may be utilized in combination with processor 1604 to provide graphical representations of aspects of the present disclosure. In addition to a display device, computer system 1600 may include one or more other peripheral output devices including, but not limited to, an audio speaker, a printer, and any combinations thereof. Such peripheral output devices may be connected to bus 1612 via a peripheral interface 1656. Examples of a peripheral interface include, but are not limited to, a serial port, a USB connection, a FIREWIRE connection, a parallel connection, and any combinations thereof.

It should be apparent from the foregoing description that various example embodiments may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles described herein. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of diagnosing a disease using a wearable device worn by a user, the wearable device having a display and wearable sensors, the wearable sensors including at least one microphone, the method comprising:
    monitoring, with the wearable device, wearable sensor data generated by the wearable sensors;
    analyzing, with the wearable device, the wearable sensor data to determine whether the user is exhibiting symptoms of a disease, the analyzing comprising comparing at least one portion of the wearable sensor data to at least one disease-specific alert setting, wherein a match of the at least one portion of the wearable sensor data to the at least one disease-specific alert setting is indicative of the user exhibiting symptoms of the disease;
    instructing the user in response to the analysis indicating that the user is exhibiting symptoms of a disease, to place the at least one microphone on a specific location on the user's body for obtaining audio data for auscultation for diagnosing whether the user has the disease, wherein the instructing includes providing a representation of a human body on the display with an indicator corresponding to the specific location on the body where the at least one microphone should be placed; and
    after instructing the user, capturing the audio data via the microphone.

2. The method according to claim 1, further comprising:
    displaying, on the wearable device display, a disease-selection user interface (UI) for displaying a plurality of diseases the wearable device may be configured to monitor for;
    receiving a user selection, via the disease-selection UI, of at least one disease for monitoring and diagnosis; and
    configuring the wearable device, based on the user selection, with the disease-specific alert settings for executing said analyzing.

3. The method according to claim 2, further comprising:
    transmitting the user selection from the wearable device to a network having a server alert database having a plurality of disease-specific alert settings corresponding to respective ones of the plurality of diseases; and
    receiving, from the server alert database, the disease-specific alert settings.

4. The method according to claim 1, further comprising:
    transmitting, with the wearable device, the audio data to a third party diagnostician device;
    receiving, with the wearable device, a diagnosis message from the third party diagnostician device; and
    displaying, on the wearable device display, the diagnosis message.

5. The method according to claim 1, wherein said instructing includes displaying, on the wearable device display, a user alert UI, the user alert UI having:
    at least one triggering data field for displaying the wearable sensor data that meets or exceeds the one or more disease-specific alert settings; and
    an alert message field for displaying an alert message for notifying the user of the disease the user is exhibiting symptoms of.

6. The method according to claim 1, wherein said instructing includes providing at least one of visual, audio, and haptic feedback with the wearable device for indicating when the at least one microphone is getting closer or getting farther away from the specific location on the user's body.

7. The method according to claim 1, wherein the wearable sensor data includes at least one of user respiration rate, user heart rate, user temperature, user blood pressure, user movement, user audio, user blood oxygen level, and user blood glucose level.

8. The method according to claim 7, further including processing, with the wearable device, the wearable sensor data to generate processed sensor data, wherein said comparing further includes comparing the processed sensor data to the one or more disease-specific alert settings.

9. The method according to claim 8, wherein said processing includes processing the user audio to identify user disease symptom sounds.

10. The method according to claim 8, wherein said processing includes generating cumulative sensor data from the sensor data and the processed data.

11. The method according to claim 8, wherein said processing includes:
    selecting an algorithm of a plurality of audio processing algorithms based on the step of analyzing, wherein the selected algorithm is associated with at least one of the disease and the specific location of the user's body; and
    applying the selected algorithm to process the user audio.

12. A wearable device for diagnosing a disease comprising:
- a display;
- wearable sensors including at least one microphone; and
- a machine-readable storage medium for storing machine executable instructions designed and configured to cause the wearable device to:
- monitor wearable sensor data generated by said wearable sensors;
- analyze the wearable sensor data to determine whether the user is exhibiting symptoms of a disease by comparing at least one portion of the wearable sensor data to at least one disease-specific alert setting, wherein a match of the at least one portion of the wearable sensor data to the at least one disease-specific alert setting is indicative of the user exhibiting symptoms of the disease;
- instruct the user, in response to the analysis indicating that the user is exhibiting symptoms of a disease, to place the at least one microphone on a specific location on the user's body for obtaining audio data for auscultation for diagnosing whether the user has the disease, wherein instructing the user includes providing a representation of a human body on the display with an indicator corresponding to the specific location on the body where the at least one microphone should be placed; and
- after instructing the user, capturing the audio data via the microphone.

13. The wearable device according to claim 12, wherein said machine executable instructions are further designed and configured to:
- display, on said wearable device display, a disease-selection user interface (UI) for displaying a plurality of diseases the wearable device may be configured to monitor for;
- receive a user selection, via the disease-selection UI, of at least one disease for monitoring and diagnosis; and
- configure the wearable device, based on the user selection, with the disease-specific alert settings for executing said analyzing.

14. The wearable device according to claim 12, wherein said machine executable instructions are further designed and configured to:
- transmit a user selection from said wearable device to a network having a server alert database having a plurality of disease-specific alert settings corresponding to respective ones of the plurality of diseases; and
- receive, from the server alert database, said disease-specific alert settings.

* * * * *